US012102711B1

(12) United States Patent
Zani

(10) Patent No.: US 12,102,711 B1
(45) Date of Patent: *Oct. 1, 2024

(54) DRUG DELIVERY SYSTEMS AND METHODS FOR MAKING AND USING THE SAME

(71) Applicant: NexGen Semi Holding, Inc., San Juan Capistrano, CA (US)

(72) Inventor: Michael John Zani, Laguna Niguel, CA (US)

(73) Assignee: NEXGEN SEMI HOLDING, INC., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,173

(22) Filed: May 22, 2023

Related U.S. Application Data

(63) Continuation of application No. 15/360,718, filed on Nov. 23, 2016, now Pat. No. 11,737,970.

(60) Provisional application No. 62/259,569, filed on Nov. 24, 2015.

(51) Int. Cl.
*A61K 9/16* (2006.01)
*A61K 9/00* (2006.01)
*B82Y 5/00* (2011.01)

(52) U.S. Cl.
CPC .................. *A61K 9/00* (2013.01); *B82Y 5/00* (2013.01); *Y10S 424/00* (2013.01)

(58) Field of Classification Search
CPC ... A61K 9/16; A61K 9/14; A61K 9/70; A61K 9/1682; A61K 9/1694
See application file for complete search history.

(56) References Cited

U.S. PATENT DOCUMENTS

| | | | | |
|---|---|---|---|---|
| 2004/0210289 | A1 | 10/2004 | Wang et al. | |
| 2004/0234604 | A1 | 11/2004 | Mecking et al. | |
| 2009/0149340 | A1 * | 6/2009 | True ................. | G01N 33/54313 506/13 |

* cited by examiner

*Primary Examiner* — Micah Paul Young

(74) *Attorney, Agent, or Firm* — Stetina Brunda Garred & Brucker

(57) ABSTRACT

During nanoscale manufacture on a substrate, payload active agents are loaded on a delivery platform, with a release layer between the delivery platform and the payload active agent and an encapsulate over the payload active agent. The combined delivery platform, release layer, active agent payload, and encapsulant form a nanoscale drug delivery vehicle for subsequent delivery to a patient. The nanoscale drug delivery vehicle is small enough to permeate through the cell and deliver the payload active agent within the cell via reducing the retaining functionality of the release layer and degrading of the encapsulant. The nanoscale drug delivery vehicle offers a series of improved features including greater control of size, shape, dosage, bioavailability, cell targeting, and release timing.

24 Claims, 4 Drawing Sheets

Side View (Cut Away)

Side View (Cut Away)

Top View

DRUG DELIVERY SYSTEMS AND METHODS FOR MAKING AND USING THE SAME

CROSS-REFERENCE TO RELATED APPLICATIONS

This Application is a continuation of U.S. application Ser. No. 15/360,718 filed Nov. 23, 2016, and entitled DRUG DELIVERY SYSTEMS AND METHODS FOR MAKING AND USING THE SAME which relates to and claims the benefit of U.S. Provisional Application No. 62/269,569 filed Nov. 24, 2015, and entitled "DRUG DELIVERY SYSTEM AND METHODS FOR MAKING AND USING THE SAME," the entire disclosures of which are hereby wholly incorporated by reference.

STATEMENT RE: FEDERALLY SPONSORED RESEARCH/DEVELOPMENT

Not Applicable

BACKGROUND

1. Field of the Invention

The present application related to nanoscale devices for use in drug manufacturing, delivery and methods for using and making the same. More specifically, the present application relates to nanoscale drug delivery vehicles and methods of preparing and administering the same.

2. Related Art

Over the past two decades, nanotechnology has opened the door to many fields resulting in exponential growth in new nanoparticle-based drugs. Current approaches to drug delivery mechanisms center on methods to improve bioavailability of a drug. Bioavailability refers to the ability to deliver and sustain high concentrations of the drug molecules at target locations, with high bioavailability being achieved by molecular targeting of particular cells within the body using nano-engineered devices to deliver drugs to the targeted cells with precision. Nanoparticles also are understood to have unusual properties that can be used to improve drug delivery due to their physical properties, including the size and shape of the drug. Where larger particles would have been cleared from the body, cells take up and adsorb nanoparticles smaller than 100 nanometers because of their size.

Complex drug delivery mechanisms have in the past been contemplated which rely on the ability of nanoscale medicines to get drugs through cell membranes and into cell cytoplasm. Efficiency in cellular uptake is important, because many diseases depend upon processes within the cell, and can only be most effectively impeded by maximizing drug concentration within the cell. Triggered response schemes are also another way for drug molecules to be used more efficiently. In these schemes, drugs are placed in the body and only activated when encountering a control signal. For example, a drug with poor solubility will be replaced by a drug delivery system where both hydrophilic and hydrophobic environments exist, improving the solubility. Another reason targeted delivery is important is because a drug may cause tissue damage. With controlled drug delivery, regulated drug release can eliminate or minimize that problem. Furthermore, if a drug is cleared too quickly from the body, this could force a patient to use high doses. With nanoscale drug delivery systems, clearance can be reduced by altering the pharmacokinetics of the drug on the molecular level, changing the administering of the drug from once per day to once per week as example. Lipid, protein and polymer-based nanoparticles can be designed to improve the pharmacological and therapeutic properties of drugs through improved delivery.

There are currently multiple techniques previously contemplated in the manufacture of nanoscale medicines, including electro nanospray, loaded carbon nanotubes, and multiple types of nanocapsules including: nanoshells, microspheres, nanopolymers, loaded micellar nanoparticles, molecular dots, and hallow silica, to name a few. These techniques, however, suffer from certain deficiencies.

For example, only a limited number of these techniques are capable of production of sub 100 nm combinatorial products via the use of an ambient manufacturing processing. Additionally, none of these currently offered techniques allow highly controlled, repeatable, and low cost manufacturing that meets the needs of today's patients for nanoscale medicines having high precision, homogenenous doses, and greater control of size and shape. Further, none of these currently offered technique provide for certain unmet needs, such as customizable loading of active drug based agents with the ability for controlled release and intracellular controlled delivery, and none offer the potential for patient-level prescription verification.

Therefore, novel nanoscale drug delivery systems and novel methods for producing these system are desirable.

BRIEF SUMMARY

To solve these and other problems, a nanoscale drug delivery vehicle and methods of forming, developing, preparing, releasing, identifying, and administering the same are contemplated. According to certain embodiments of the present disclosure, it may be seen that aspects of this new drug delivery vehicle may permit both research and manufacture of high volumes of highly purified, highly potent and freshly manufactured on-demand personalized drugs, hybrid drugs, custom deliverable medicines, supplements, vaccines, therapeutics, combinatorial generic medicines, fertilizers, lubricants and specialty detergents. It may be additionally be seen that certain aspects of these or other embodiments of the present disclosure may be utilized by clinicians or researchers to meet unsolved needs in the fields of nanotoxicology, genomics, proteomics, lipid or polymer-based nanoparticles, carrier-mediated chemotherapeutic agents, selective active or passive delivery methods, antibiotics, nano based anti-cancer and anti-aging agents. It may further be seen that certain aspects of these and other embodiments may result in the formulation of drugs having improved biodistribution, and may permit the delivery of personalized pharmacokinetics medicine having improved pharmacodynamics and bioavailability within the cell.

The nanoscale drug delivery vehicle contemplated herein, which is a nanoscale sized structure, allows the deposit and adhesion, encapsulation, transportation, controlled release and delivery of payload active agents, which are medicines bound to a controlled release layer as nanoscale size payloads on the nanoscale size platforms to be delivered in vivo or in vitro to the body or living organism. The payload active agents referenced include, but are not limited to, a pharmaceutical drug, a biological molecule, a lipid, a carbohydrate, a polymer, an amino acid, a polymeric drug, a protein, a nucleic acid, a combinatorial polymer, a lipoid, a fatty acid, a wax, a steroid, a vitamin, a glyceride, a liquid, a crystal, an electronic nanostructure, an element, a compound, an antibiotic, a vaccine, a genomic agent, virus, mitochondria, bacteria, a physical structures, a detergent, a lubricant, a fertilizer, a therapeutic, nucleotide, nucleoside, a supplement, a combinatorial medicine, a nano-machine, a cosmetic, a marker, a solvent, or combinations thereof, which may include a plurality of each, combination subsets, or complete solutions of each.

The nanoscale drug delivery vehicles are produced on a substrate with a buffer layer material disposable between the substrate and the delivery platform, a release layer material disposable between the delivery platform and the payload active agent, with the payload active agent being covered with a protective encapsulant layer material. The buffer layer, release layer and encapsulant layer materials are each selected in order to control separation of the respectively bound or encapsulated components during transfer to the target host. The buffer layer is a thin film material disposable between the substrate and the delivery platform that is configured to adhere the delivery platform to the substrate and is further configured to subsequently permit the release of the delivery platform from the substrate via a process configured to avoid destroying the functionality of the payload active agent. The release layer is a thin material disposable between the platform and the active agent used to control separation of the payload active agent from the delivery platform without destroying the functionality of the payload active agent. The encapsulant layer is a protective layer, allowing a 2D or 3D build of material, hybrid material, or combinations thereof, plus serving as a protective coating used during travel to protect the transfer of payload active agents from the substrate to the delivery mechanism to the target host, or within the host.

Together, the delivery platform, release layer, payload active agent, and encapsulant comprise the nanoscale drug delivery vehicle. Certain embodiments disclosed herein pertain to methods for the formulation and/or for mass production of micro- and nanoscale nanoparticle-based drug delivery vehicles. According to certain of these embodiments, the micro- and nanoscale drug delivery vehicle comprise one or more micro- and nanoparticle delivery platform. In some embodiments, the micro or nanoscale nanoparticle-based drug delivery vehicle comprises one or more medicines on each delivery platform. In some embodiments, the nanoscale drug delivery vehicle comprises one or more active or passive release mechanisms. In some embodiments, the nanoscale drug delivery vehicle comprises one or more passive or active buffer mechanisms.

According to other embodiment, it is also contemplated that the nanoscale drug delivery vehicle and its methods of manufacture may omit the delivery platform, and instead comprise the active agent payload and the encapsulant.

All of these embodiments are contemplated to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features and advantages of the various embodiments disclosed herein are better understood with respect to the following descriptions and drawings, in which.

DETAILED DESCRIPTION

Figure 1:
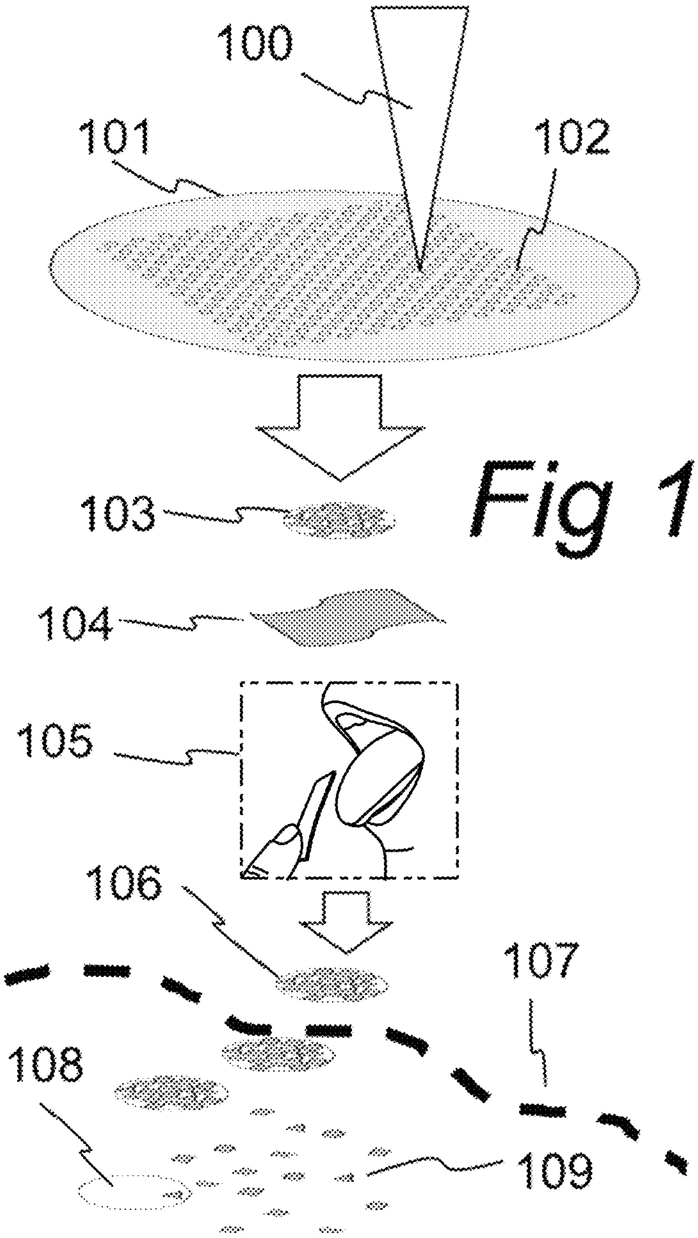
FIG. 1 is a perspective view of an example manufacture of nanoscale medicine loaded on platform, with an example release from the substrate to adhesive, delivered to the body, permeating through the cell and payload medicines released within the cell.

Disclosed herein are nanoscale based drug delivery vehicles and methods for researching, developing, manufacturing, preparing, and administering the same. According to the preferred embodiment, the drug delivery platform is a nanoscale-sized structure that allows the deposit and adhesion, encapsulation, transportation, controlled release and delivery of nanoscale-size payload active agents which are medicines bound to the delivery platform by a controllable release layer for delivery in vivo or in vitro to a patient or other biological specimen.

In some aspects, the nanoscale drug delivery vehicles are prepared by printing therapeutic payload active agents on nanoscale delivery platforms. In some aspects, the nanoscale drug delivery vehicles are prepared by means of three dimensional printing on delivery platforms. In some aspects, the delivery platforms are active structures (e.g., they have some therapeutic effect on their own). In some aspects, the delivery platforms improve and/or control bioavailability of therapeutics (e.g., peptide drugs, pharmaceutical drugs, biomolecules, etc.)-a key factor in drug delivery. In some embodiments, the concept disclosed herein uses surface exposure using a beam of particles to seed growth areas to custom deposit sub-30 nanometer payload active agents (e.g., therapeutics) onto sub-100 nanometer disks (e.g. platforms, platform islands, etc.) that are taken up by the cell when introduced into the body or cell transdermally, intradermally, intravenously, topical, transmucosally, orally, as a suppository, ocularly, through the respiratory system or direct surface contact, as a liquid, as a powder, a dissolvable tape, as a non-dissolvable tape, as a compact pill, as a capsule or as a combination of one or plural combination of more than one for in vitro or in vivo delivery to the body or cell. In some aspects, the disposing of the payload active agents is by means of surface nucleation deposition, atomic layer deposition, physical vapor deposition, chemical vapor deposition, evaporation deposition, plasma deposition, electroplating or chemically assisted particle beam deposition.

In some aspects, the largest dimension of the deposited payload active agent is less than about 500 nm, about 100 nm, about 50 nm, about 40 nm, about 30 nm, about 20 nm, or about 10 nm in diameter, measured at the widest point. In some embodiments, the largest dimension of the delivery platform is less than about 1000 nm, about 100 nm, about 80 nm, or about 50 nm in diameter, measured at the widest point. The nanoscale drug delivery vehicles containing the payload active agent may be printed in batches of similar or dissimilar sizes, and in similar or dissimilar shapes, all of which may be seen to affect intracellular permeability, solubility and bioavailability of the nanoscale drug delivery vehicles and/or the payload active agents. the nanoscale drug delivery vehicles may be printed using techniques including, but not limited to, resist based optical lithography, direct-write particle beam lithography; imprint patterning, directed self-assembly or resistless nucleation patterning.

It may be seen that one aspect of the present disclosure is that patterning of the material, including the material comprising the delivery platform and the payload active agent, at the nanoscale level, may allow the ability to create sub-wavelength surface metastructures of the payload active agent and/or the delivery platform. These patterned metastructure features allow custom or semi-custom printing of single and/or multiple reflective signatures, which may be utilized according to known and future methods of optical and/or other form of verification to allow up to patient-level verification of manufacturer origin, time, lot code and prescription, as well as to convey any and all other forms of encoded information for useful purposes throughout the manufacturing, prescribing, administering, and potentially even the post-administration process. According to various embodiments, the method of preparing the nanoscale drug delivery vehicle, including the provision of the materials used in forming the nanoscale drug delivery vehicle, and the disposing of those materials to form the components used in its manufacture, including but not limited to the substrate, the buffer layer, the release layer, the delivery platform, the payload active agent, and the encapsulant layer may be performed by various known and future developed methods, which may include but are not limited to nucleation deposition, atomic layer deposition, physical vapor deposition, chemical vapor deposition, evaporation deposition, electroplating, ink printing, chemically assisted particle beam deposition, a combination or a subset of each process with the emphasis of ambient temperature, pressure and chemical exposure for each process to avoid destroying the active agent payload.

Once produced, the nanoscale drug delivery vehicle structure, which according the preferred embodiment comprises the delivery platform, the payload active agent, the release layer, and the encapsulant, may be removed from the substrate using a variety of techniques to reduce the buffer layer's retaining functionality, which may include known and future developed methods, including but not limited to thermal exposure, chemical exposure, sound exposure, electromagnetic field exposure, light exposure, and mechanical force. For example, according to the one contemplated embodiments, the nanoscale drug delivery vehicle may be physically adhered to a second object, such as a liftoff structure, and the delivery platform of the nanoscale drug delivery platform may be released from the substrate via physical force. According to other embodiments, release of the nanoscale drug delivery platform from the substrate may be achieved via the buffer layer being dissolved in a solution, transferring the nanoscale drug delivery vehicle structures to the solution. According to further embodiments, the nanoscale drug delivery vehicle may be release from the substrate according and be collected in an evaporated dry powder form. However, it may be seen that once released from the substrate, the nanoscale drug delivery vehicles may be collected in any known or future developed form in which nanoscale structures are collected, and as such may be packaged, administered, or otherwise further manipulated in known or future developed ways.

According to a preferred embodiment, the nanoscale drug delivery vehicles may be embedded within a dissolvable or non-dissolvable tape, bandage or implantable physical structure as a deliverable media. Each individual unit of a deliverable media of these types may have, for example, between hundreds of thousands to trillions of individual nanoscale drug delivery vehicles per unit. Delivery mechanisms to administer the nanoscale drug delivery vehicles may include all known or future developed methods of administration, including but not limited to administration transdermally, intradermally, intravenously, topical, transmucosal orally, as a suppository, ocular, respiratory or direct surface contact transfer, and my include all known or future forms of administrable compounds, including but not limited to liquids, powders, populated surfaces by means of a liquid or a powder, a dissolvable tape, a non-dissolvable tape, a compact pill, a capsule or a combination of one or plural combination of more than one for in vitro, or in vivo delivery to a patient or biological specimen.

In some embodiments, these nanoscale drug delivery vehicles have the potential to turn molecular discoveries arising from generic and advanced therapeutic drug development into widespread benefit for patients. In some aspects, the nanoscale drug delivery vehicles offer improved delivery systems for existing drugs that can be manufactured on-demand, as a customizable, on-demand activation medical solution for each individual patient.

In some embodiments, the nanoscale drug delivery vehicles may be configured to have a controlled release of one or more of the payload active agents into the patient or biological specimen to which it is or will be administered, with such controlled release being controlled by known or future developed methods that may be influenced or controlled by certain controllable aspects of the nanoscale drug delivery vehicle and the components thereof, such as shape, size, magnetic properties, electric field properties charge doping, and other aspects. It may be seen that manipulation of such aspects may affect the bioactive characteristics of the payload active agents nanoscale drug delivery vehicles, including but not limited to active or passive bioavailability. In some aspects, the release of the payload active agents loaded on the nanoscale drug delivery vehicles may allows passive or active triggered release through mechanisms based upon thermal, time, sound, light, magnetic, electric field, or radiation, all of which may affect bioavailability characteristics within the body or within the cell. In some aspects, intracellular delivery of multiple nanoscale drug delivery vehicles or their payload active agents may allow recombination or reconstruction of the payload active agents to form ideal therapeutics that are too large to permeate the cell as originally designed.

In some embodiments which target efficiency in biodistribution, the nanoscale drug delivery vehicles may has dimensions of less than about 500 nm, about 200 nm, about 100 nm, about 90 nm, about 80 nm, about 70 nm, about 50 nm, about 30 nm about 10 nm, about 1 nm, or about 0.5 nm in diameter, measured at the widest point, In some aspects, the nanoscale drug delivery vehicles prepared according to the disclosed methods may be small enough to penetrate the cell wall/membrane. In some aspects, the nanoscale drug delivery vehicles and/or payload active agents prepared by the disclosed methods are variously configured to improve bioavailability, require lower doses than conventional forms of drugs via conventional methods of administration, and to selectively target delivery zones within the body.

In some embodiments, the nanoscale drug delivery vehicles are prepared using "direct-write" technologies, massively parallel particle beam printing technologies, optical lithography printing technologies, nano imprint technologies, directed self-assembly (DSA) technologies or a combination of one or more of these technologies. However, it may be seen that the nanoscale drug delivery vehicles may be formed according to other known and future developed methods of preparation. According to one particular embodiment, a method of preparing a nanoscale drug delivery vehicles is contemplated in which a beam technology it utilized, which may be seen to result in high speed, high resolution (resistless) pattern processing for heterogeneous patterned deposits. According to the preferred embodiment, the nanoscale drug delivery vehicles may be prepared according to the systems and methods for operation of the various embodiments of the direct-write and particle beam printing technologies disclosed in the following U.S. Patents, the disclosure of each of which are hereby incorporated by reference: U.S. Pat. Nos. 7,259,373; 7,993,813; 7,501,644; 7,495,244; 7,507,960; and 7,659,526.

In some embodiments, the nanoscale drug delivery vehicles prepared using the methods disclosed herein may fully customize the delivery platform, the payload active agent, or both for generic or patient specific application. In some aspects, one or more materials can be used as a platform (e.g., scaffold, support, matrix, platform, etc.) or buffer to result in positive or negative adhesive. In some embodiments, one or more of the payload active agents can be formed having a patterned metastructure. In some embodiments, by leveraging the ability to make unique "direct-write" sub-100 nanometer structures, using the chemical purity of the semiconductor industry, and new beam technologies for high speed, high resolution (resistless) pattern processing, the high volume of personally customized nanoscale drug delivery vehicles may be achieved.

In some embodiments, the nanoscale drug delivery vehicles may be manufactured by a simple selective pattern nucleation of the materials combined with encapsulating and followed by release of nanoscale drug delivery vehicles from the substrate. In some embodiments, the methods for selective pattern nucleation of the materials cannot be performed using semiconductor techniques due to the chemical and/or thermal exposure related to the resist-based fabrication. In some embodiments, resist-based fabrication would destroy the payload active agent. In some embodiments, the method for selective pattern nucleation of the material may be gentle and ambient process to avoid damaging the payload active agent or reducing their therapeutic functionality. In some embodiments, the high-speed beam and patterned processing technology can be used for manufacturing both the material of the delivery platform and of the payload active agents. In some embodiments, these nanoscale drug delivery vehicle design leverages commercial semiconductor process design software and design rule to create and design new drugs and combinations of therapeutics, supplements, genomics, and active delivery machines According to certain aspect of the present disclosure, the nanoscale drug delivery vehicles and/or the components thereof may be manufactured using ion, neutron, electron or photon beam technology, herein referred to "beam technology." It may be seen that beam technology may enables the high volume printing of the seed layer for growing one or more components of the structure of the nanoscale drug delivery vehicle. In some embodiments, the beam technology is comprised of a unique high speed ion optic, parallel beam optic or stencil projection particle beam optic that delivers spatially and temporally resolved, highly controlled, and highly repetition beam packets that improve spatially resolved interaction at the pattern seeding surface.

In some embodiments, the technology disclosed herein can leverage the maturity and flexibility of direct-write semiconductor lithography with custom 3D print nanoscaled medication preparation as a new form of customizable drug manufacturing technology. In some embodiments, the techniques described herein create a low-cost manufacturing process. In some embodiments, the fabrication can be used with computer-aided-design (CAD) information to provide 2D and 3D printed medicine allowing customizability. In some embodiments, the processes allow available-on-demand medication that can be stored in raw material and/or that can be offered at lower cost handling of bio material. In some contemplated embodiments, the nanoscale drug delivery vehicles may enable transport of drug payload active agents through the cell membranes and into the cell cytoplasm offering improved bioavailability and bio-distribution. In some embodiments, the nanoscale drug delivery vehicle and/or the components thereof, such as the delivery platform, may be formed of metal composites which can be selected, sized and conjured in order to selectively target certain organs. In some embodiments, selective targeting can be performed by adding targeting molecules to the disclosed nanoscale drug delivery vehicles. In some embodiments, selective targeting can allow improved delivery for a range of applications such as, for example, but without limitation, binding polymers to calcium for bone cancer treatment, cure infections of burn victims, or treating renal and liver failure.

3D printing has recently taking a lead role as a potential solution for future manufacturing of solid, physical and functional objects. However, there are still many problems and limitations to the technology for high resolution and high throughput manufacturing. Current limitations of the technology bar the manufacturing of hybrid materials (customizable, multi-materials, alloys and compounds), require touch (finishing) labor, and display insufficient purity for drug manufacturing and limited resolution derived from the thermal dynamics of the writing beam that creates a weld (heat) pool around the 3D feature exposure. In some embodiments, the techniques disclosed herein address those limitations.

In some embodiments, formation of surface metastructures as flat lens reflective optics can be created by the nanoscale drug delivery vehicle structure, including but not limited to the metastructure of the delivery platform or the payload active agent. It may thus be seen that these metastructures may be configured in order to convey information, which may be harnessed in order to, for example but without limitation, provide custom trusted and patient verifiable anti-counterfeit signatures.

In some embodiments, the nanoscale drug delivery vehicles are manufactured by direct write ion exposure to seed the surface substrate or delivery platform. In some embodiments, after direct write ion exposure, heterogeneous nucleation deposition is performed. In some embodiments, the process is performed by disposing a releasable buffer layer (such as an oxide or resist) on the substrate, which may be, in the exemplary embodiment, a silicon wafer. In some embodiments, delivery platforms are then disposed onto the substrate. In some embodiments, a wide range of elements, metals, composites, and alloys, can be used to form the delivery platform of the nanoscale drug delivery vehicle. In some embodiments, these delivery platforms, may be, including but without limitation, gold, aluminum, titanium, titanium dioxide, copper or zinc oxide. It may thus also be seen that the material of the delivery platform itself may also provide natural or dual function antibiotic properties, such as for example the recognized antimicrobial properties of copper. In some embodiments, the sites for the delivery platforms are exposed as circular or otherwise defined shapes on the substrate (oval, rectangular, polygonal, triangular, etc.). In some embodiments, the substrate is placed in a nucleation chamber for parallel nucleation by means of a carrier gas and de-absorption of a metal on the buffer layer. In some embodiments, the process can then be repeated with various buffers and payload layers using a variety of chemicals which are then coated with a protective layer to form an encapsulant, allowing a 2D or 3D build of material, hybrid material, systems or combinations plus a protective coating used during travel from the substrate to the delivery mechanism, with example aspects, but not limited to mechanisms as a liquid, a powder, a dissolvable tape, a non-dissolvable tape, a compact pill, a capsule or a combination of one or plural combination of more than one, in vitro or in vivo to the body or host cell.

In some embodiments, the delivery mechanism is a liquid, a powder, a dissolvable tape, a non-dissolvable tape, a compact pill, a capsule or a combination of one or plural combination of more than one.

In some embodiments, the substrate is a semiconductor wafer, including but not limited to silicon, gallium arsenide, sapphire and other common wafer materials. In some embodiments, the substrate is a less common wafer like substance, including a metal, an alloy, glass, quartz, or combinations of common and less common materials.

In some embodiments, because the disclosed methods can involve a direct write process, each nanoscale drug delivery vehicle or group of nanoscale drug delivery vehicles can be custom fabricated specifically for a patient or group of patients to maximize a unique biodistribution for that patient or group of patients.

In some embodiments, features of the presently disclosure allow the ability to both research and manufacture high volumes of high purity, highly potent and freshly manufactured on demand personalized drugs, hybrid drugs, custom deliverable medicines, supplements, vaccines, therapeutics or combinatorial generic medicines. Some embodiments permit clinicians or researchers to explore nanotoxicology, genomics, proteomics, lipid or polymer-based nanoparticles, carrier-mediated chemotherapeutic agents, selective active or passive delivery methods, antibiotics, nano based anticancer and anti-aging agents. In some embodiments, features of this new technology allow improvement of biodistribution, delivery of personalized pharmacokinetics medicine, exploration of pharmacodynamics, and how they relate to improved bioavailability by drug delivery within the cell.

Turning now to FIG. 1, a perspective view of an exemplary embodiment of a manufacturing method of a nanoscale drug delivery vehicle is shown, illustrating an example of release of the nanoscale drug delivery vehicle from the substrate to an adhesive, delivery to the body, permeation through the cell, with the payload active agents being released within the cell. According to this exemplary embodiment, the beam 100 provides localized surface disruption for patterned nucleated growth that is performed sequentially on the substrate 101 to grow the nanoscale drug delivery vehicles 102. The nanoscale drug delivery vehicle 102 are then released 103 and transferred to a deliverable media 104, which in the illustrated exemplary embodiment is dissolvable tape, which is then administered to the patient 105. Once in the patient, the nanoscale drug delivery vehicles can permeate 106 through cells 107, whereupon they may release the payload active agents 109 from the delivery platform 108.

Figure 2:
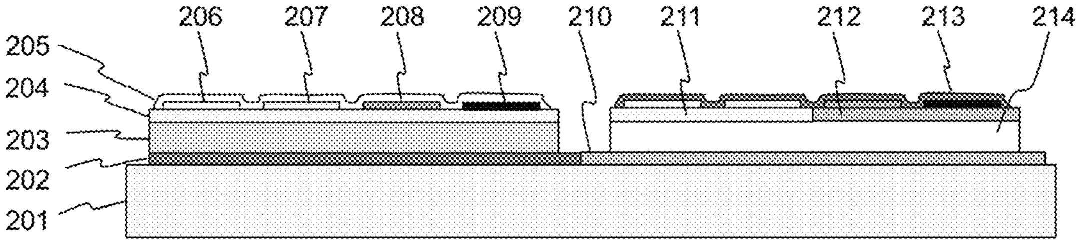
FIG. 2 is a perspective side view of an example nanoscale medicine loaded platform on substrate.

Turning now to FIG. 2, a perspective side view is shown of examples of a manufacturing method of nanoscale drug delivery vehicle on substrate according to certain embodiments disclosed herein. The components involved in the illustrated exemplary manufacturing process of the nanoscale drug delivery vehicles system comprises a substrate 201, a buffer layer 202, a delivery platform 203, a release layer 204, an encapsulant layer 205, and a plurality of payload active agents (206-209). Although not illustrated, it will be understood that the a single substrate 201 may have formed on it a single or a plurality of a nanoscale drug delivery vehicle which may comprise a delivery platform 203 and/or payload active agents 206-209. Each nanoscale drug delivery vehicle may be optionally formed with one or more buffer layers 202, one or more release layers 204, and one or more encapsulant layers 205. Illustratively, each substrate can have formed upon it nanoscale drug delivery vehicles having delivery platforms 203, 214 of formed of different materials, buffer layers 202, 210 of different material, release layers 204, 213 of different materials, and payload active agents 206-209 of different materials. It may further be seen that all of the aforementioned features of the nanoscale drug delivery vehicles and its methods for manufacture may also be vary on the same in size, shape, configuration, and other characteristics as well, whether formed on the same substrate or on different substrates.

Figure 3:
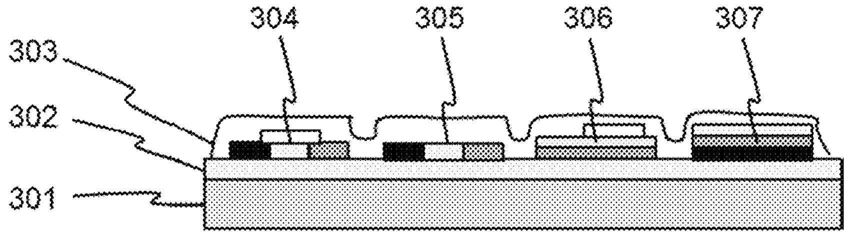
FIG. 3 is a perspective side view of an example multi drug loaded on single nano scale platform.

Turning now to FIG. 3, a perspective side view of an example of a plurality of payload active agents 304-307 loaded on single nano scale platform is shown. The payload active agents may be seen to include a variety of materials which may also be configured in a variety of configurations, including along the vertical axis as in payload active agent 307, along the horizontal axis as in payload active agent 305, in a combination of the vertical and horizontal axis as in payload active agent 304, or in variation in volume of individual materials as in payload active agents 304, 306. Although in the illustrated embodiment, delivery platform 301 is shown with a release layer 302 between it and the payload active agents 304-307, and an encapsulant layer 303 over the payload active agents 304-307, is shown, it may be understood that there may additionally be an absence of or a plurality of release layers 302 and absence of or plurality of encapsulant layers 303, and that these layers may be configured in multiple dimensions and along various axis as well.

Figure 4:
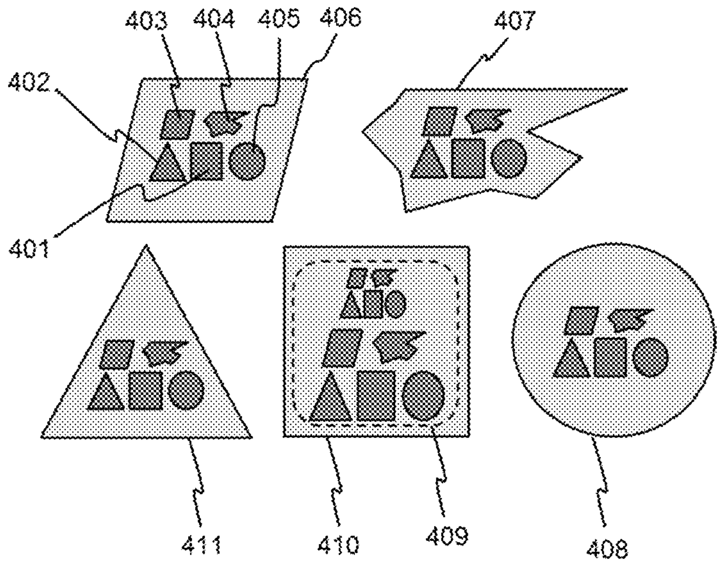
FIG. 4 is a perspective top view of an example group of multi drug loaded nanoscale platforms.

Turning now to FIG. 4, a perspective top view of an example group of nanoscale drug delivery vehicles 406, 407, 408, 410, and 411 is shown. Each nanoscale drug delivery vehicle 406, 407, 408, 410, and 411 may have an identical size and/or shape, or may have a variety of sizes and shape. Each payload active agent 401-405 deposited on the delivery platform may also have and identical and/or shape, or a variety of sizes and/or shapes.

Figure 5:
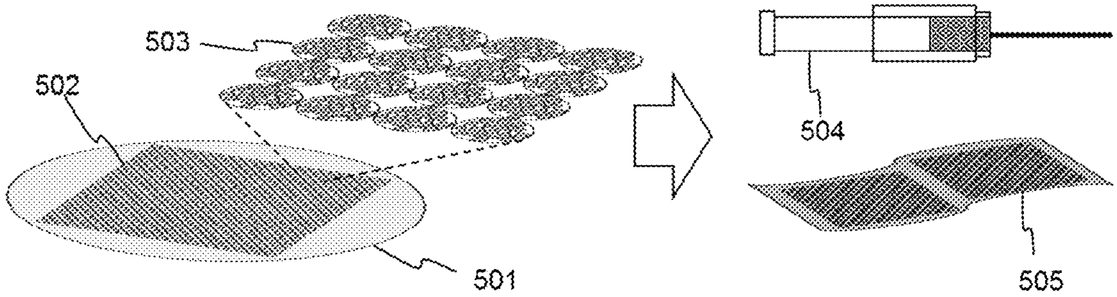
FIG. 5 is a perspective of the substrate with platforms that are loaded with deposited drugs and transferred for delivery into the body or cell.

Turning now to FIG. 5, a perspective view of an exemplary process for manufacture and preparation for administration of the nanoscale drug delivery vehicles is shown. It may be seen that a substrate 501 contains delivery platforms 502 that are loaded with active agents. The delivery platforms 502 are then released off the substrate as nanoscale drug delivery vehicles 503, and may then be transferred to a syringe 504 or dissolvable tape or skin strip 505. Although not illustrated, it will be understood that the transfer to a liquid or powder allows the nanoscale drug delivery vehicles 503 to be administered to the body or cell transdermally, intradermally, intravenously, topical, transmucosal orally, as a suppository, ocular, through the respiratory system or direct surface contact, as a liquid, as a powder, as a dissolvable tape, as a compact pill, a capsule or a combination of one or plural combinations of more than one for in vitro or in vivo delivery into the body or cell.

Figure 6:
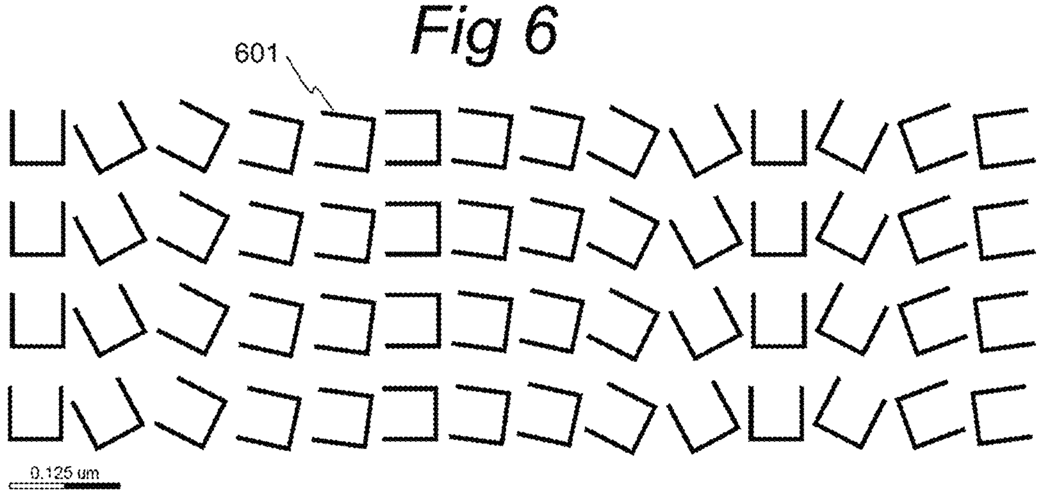
FIG. 6 is a perspective of example active agents patterned on the platform as surface metastructures to provide visible reflective signature identification.

Turning now to FIG. 6, a perspective view of an exemplary embodiment of a surface metastructures is shown. It may be understood that the material of the delivery platforms or the arrangement of the payload active agents may be configured in such a metastructure so as to provide visible reflective signature identification by patterning the material 601. In the illustrated embodiment, the patterned material 601 is configured to repeat in subwavelength structures that allow group reflectance at frequency bands which may be visible to the patient, conveying information.

A wide variety of variations are possible. Components may be added, removed or reordered. Different components may be substituted out. The arrangement and configuration may be different. Similarly, processing steps may be added or removed, or reordered.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

It will further be appreciated that applications for this disclosure are virtually unlimited. Described above are a small number of high leveraged nanomedicine applications to demonstrate the potential of this disclosure, particularly for controlled delivery of protein and lipid loaded nanomedicines. A wide variety of other application are possible. It will be further appreciated that the majority of the disclosed method steps can also be performed via existing resist based semiconductor patterning using optical lithography. This may be seen as equivalent to present day technology and may greatly reduce the risk of various steps.

Although this disclosure is generally in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In addition, while several variations of the various embodiments disclosed herein have been shown and described in detail, other modifications, which are within the scope of this disclosure, will be readily apparent to those of skill in the art. It is also contemplated that various combinations or sub-combinations of the specific features and aspects of the disclosed embodiments can be combined with, or substituted for, one another in order to form varying modes. Thus, it is intended that the scope of the present disclosure should not be limited by the particular disclosed embodiments described above, but should be determined only by a fair reading of the claims that follow.

What is claimed is:

1. A method of preparing a nanoscale drug delivery vehicle for drug delivery to a patient or biological specimen, the method comprising the sequential performance of the steps of:

(a) providing a substrate;

(b) disposing a buffer layer onto the substrate;

(c) disposing a delivery platform onto the buffer layer;

(d) disposing a release layer onto the delivery platform; and (e) disposing a payload active agent onto the release layer;

wherein the payload active agent, the release layer, the delivery platform, the buffer layer, and the substate are configured in vertical alignment along a vertical axis, with the payload active agent being disposed above the release layer along the vertical axis, the release layer being disposed above the delivery platform along the vertical axis, the delivery platform being disposed above the buffer layer along the vertical axis, and the buffer layer being disposed above the substrate along the vertical axis;

wherein the buffer layer retains the delivery platform against the substrate;

wherein the release layer retains the payload active agent against the delivery platform;

wherein following the sequential performance of steps (a) through (e), the nanoscale drug delivery vehicle, comprising the delivery platform, the release layer, and the payload active agent, is prepared via releasing the delivery platform from the substrate via reducing the buffer layer's retaining functionality.

2. The method of claim 1, wherein the buffer layer is absent.

3. The method of claim 1, wherein the delivery platform is absent.

4. The method of claim 1, wherein the release layer is absent.

5. The method of claim 1, wherein the nanoscale drug delivery vehicle is below 300 nanometers in size.

6. The method of claim 1, further comprising a step of disposing a release layer between the substrate and the active agent for controlling the release of the active agent against the substrate.

7. The method of claim 1, further comprising a step of releasing the active agent from the delivery platform via reducing the release layer's retaining functionality via one or more of: thermal exposure, chemical exposure, sound exposure, electromagnetic field exposure, light exposure, mechanical force.

8. The method of claim 1, wherein any of the layers comprises one or more of the group of: a pharmaceutical drug, a biological molecule, a lipid, a carbohydrate, a polymer, an amino acid, a polymeric drug, a protein, a nucleic acid, a combinatorial polymer, a fatty acid, a combinatorial therapeutic, a wax, a steroid, a glyceride, a liquid, an element, a compound, an antibiotic, a vaccine, a genomic agent, a virus, mitochondria, a bacteria, a physical structure, a detergent, a lubricant, a fertilizer, a therapeutic, a nucleotide, a nucleoside, a supplement, a combinatorial medicine, a nano machine, a cosmetic, a marker, a solvent.

9. The method of claim 1, wherein the step of depositing is performed via one or more of nucleation deposition, atomic layer deposition, polymer spin coating, vapor deposition, plasma deposition, chemical vapor deposition, chemically assisted particle beam deposition, plasma deposition, electroplating.

10. The method of claim 1, wherein one or more of the steps of disposing a layer onto the substrate or disposing the payload active agent onto the delivery platform comprise patterning via a nanoscale manufacturing technique chosen from one or more of: direct writing, optical lithography, directed self-assembly, imprint lithography, particle beam lithography, patterned additive manufacturing.

11. A method of preparing a nanoscale drug delivery vehicle for drug delivery to the body or biological specimen, the method comprising the sequential performance of the steps of:

providing a substrate;

disposing a payload active agent onto the substrate; and releasing the payload active agent from the substrate.

12. The method of claim 11, wherein the step of disposing the payload active agent onto the substrate is performed via one or more of: nucleation deposition, atomic layer deposition, polymer spin coating, vapor deposition, plasma deposition, chemical vapor deposition, chemically assisted particle beam deposition, plasma deposition, electroplating.

13. The method of claim 12, further comprising a step of disposing a buffer layer between the substrate and the payload active agent for retaining the payload active agent against the substrate.

14. The method of claim 13, wherein the step of disposing the buffer layer between the substrate and the payload active agent is performed via one or more of: nucleation deposition, atomic layer deposition, polymer spin coating, heating of the substrate, vapor deposition, plasma deposition, chemical vapor deposition, chemically assisted particle beam deposition, plasma deposition, electroplating.

15. The method of claim 14 further comprising a step of releasing the active agent from the substrate via reducing the buffer layer's retaining functionality via one or more of: thermal exposure, chemical exposure, sound exposure, electromagnetic field exposure, light exposure, mechanical force.

16. The method of claim 15, wherein upon releasing the payload active agent from the substrate, the payload active agent is adhered to a second object.

17. The method of claim 11, further comprising a step of disposing an encapsulant over the active agent.

18. The method of claim 17, wherein the encapsulant is formed of a material comprising one or more of: a solvent, a polymer, a wax, a fatty acid, an amino acid, a protein, an enteric coating, a protective active agent, a shellac.

19. The method of claim 17, further comprising a step of exposing the active agent from under the encapsulant by degrading the encapsulant via one or more of: thermal exposure, chemical exposure, sound exposure, electromagnetic field exposure, light exposure, mechanical force.

20. The method of claim 11, wherein the payload active agent comprises one or more of the group of: a pharmaceutical drug, a biological molecule, a lipid, a carbohydrate, a polymer, an amino acid, a polymeric drug, a protein, a nucleic acid, a combinatorial polymer, a fatty acid, a combinatorial therapeutic, a wax, a steroid, a glyceride, a liquid, an element, a compound, an antibiotic, a vaccine, a genomic agent, a virus, mitochondria, a bacteria, a physical structure, a detergent, a lubricant, a fertilizer, a therapeutic, a nucleotide, a nucleoside, a supplement, a combinatorial medicine, a nano machine, a cosmetic, a marker, a solvent.

21. The nanoscale drug delivery vehicle of claim 1, wherein the nanoscale drug delivery vehicle is contained within one or more of: a liquid, a powder, a dissolvable tape, a non-dissolvable tape, a gas, a compact pill, a capsule.

22. The method of claim 20, wherein the nanoscale drug delivery vehicle is administered according to a method chosen from one or more of: transdermal, intradermal, subcutaneously, intramuscularly, intravenously, ocularly, in vitro, in vivo, through the respiratory system, administered to direct surface contact, delivered as a liquid, delivered as a powder.

23. The method of claim 22, where in the administration of the nanoscale drug delivery vehicle is operative to facilitate treatment of a disease.

24. The method of claim 23, wherein the treatment of a disease comprises controlling the release of the payload active agent from the nanoscale drug delivery vehicle within the body or biological specimen following administration of the nanoscale drug delivery vehicle.

* * * * *